United States Patent
Musa et al.

(10) Patent No.: US 6,930,136 B2
(45) Date of Patent: Aug. 16, 2005

(54) ADHESION PROMOTERS CONTAINING BENZOTRIAZOLES

(75) Inventors: Osama M. Musa, Hillsborough, NJ (US); Harry Richard Kuder, Fullerton, CA (US)

(73) Assignee: National Starch and Chemical Investment Holding Corporation, New Castle, DE (US)

(*) Notice: Subject to any disclaimer, the term of this patent is extended or adjusted under 35 U.S.C. 154(b) by 460 days.

(21) Appl. No.: 09/966,453

(22) Filed: Sep. 28, 2001

(65) Prior Publication Data

US 2003/0098440 A1 May 29, 2003

(51) Int. Cl.[7] .................................................. C08K 5/24
(52) U.S. Cl. ........................ 524/91; 548/257; 548/260; 548/261; 548/517; 548/518; 548/519; 548/523; 548/524
(58) Field of Search ............................ 524/91; 548/257, 548/260, 261, 517, 518, 519, 523, 524

(56) References Cited

U.S. PATENT DOCUMENTS

| | | | |
|---|---|---|---|
| 3,004,896 A | 10/1961 | Heller | |
| 3,493,539 A | 2/1970 | Skouitchl et al. | 260/47 |
| 4,428,987 A | 1/1984 | Bell et al. | 427/327 |
| 4,448,847 A | 5/1984 | Bell et al. | 428/413 |
| 4,996,326 A * | 2/1991 | Leppard | 548/261 |
| 5,122,858 A | 6/1992 | Mahulikar et al. | 357/70 |
| 5,449,951 A | 9/1995 | Parthasarathi et al. | 257/677 |
| 5,627,227 A * | 5/1997 | Suga et al. | 524/91 |
| 6,166,218 A * | 12/2000 | Ravichandran et al. | 548/257 |
| 6,225,378 B1 | 5/2001 | Wang et al. | 523/454 |

FOREIGN PATENT DOCUMENTS

| | | | |
|---|---|---|---|
| DE | 44 36 355 A1 | 6/1995 | |
| DE | 197 48 658 A1 | 5/1998 | |
| EP | 0 251 490 | 5/1987 | |
| EP | 0 251 490 A2 | 5/1987 | C09J/5/02 |
| EP | 0 285 266 A3 | 3/1988 | C08J/5/12 |
| EP | 0 285 266 A2 | 3/1988 | C08J/5/12 |
| EP | 0 285 266 | 4/1988 | |
| EP | 0 431 868 | 3/1990 | |
| EP | 0 736 577 | 3/1996 | |
| EP | 0 970 946 | 1/1999 | |
| EP | 1 033 590 | 2/2000 | |
| EP | 1 033 590 A2 | 2/2000 | G02B/1/04 |
| FR | 1325404 | 6/1962 | |
| FR | 1330378 | 6/1962 | |
| FR | 1330379 | 6/1962 | |
| FR | 2122465 | 1/1972 | |
| JP | HEI 11-1999-195358 | 7/1999 | |
| JP | HEI 11-1999-196722 | 7/1999 | |
| JP | HEI 11-1999-285892 | 10/1999 | |
| JP | 2000096032 | 4/2000 | |

OTHER PUBLICATIONS

Yoshida, S. et al.: "Functional Polymers. XII[a,b]: Synthesis and Polymerization of 2–Vinyl–4–hydroxyphenyl)2 H benzotriazole and 2(3–Vinyl–4–hydroxyphenyl)2 H–benzotriazole"; Monatshefte fur Chemie 113, 603–622 (1982).

Shanjun, L . . . et al.: "Synthesis of Compounds with More than One Benzotriazole Group in the Molecule"; Monatshefte fur Chemie 114, 937–891 (1983).

(Continued)

*Primary Examiner*—Cephia D. Toomer
(74) *Attorney, Agent, or Firm*—Jane E. Gannaro

(57) ABSTRACT

Benzotriazole adducts contain a benzotriazole segment and a segment with a curable and polymerizable functionality, or an adhesion promoting functionality, particularly suitable for use on metal substrates or in adhesive, sealant or coating compositions for use in proximity to metal substrates.

9 Claims, 1 Drawing Sheet

OTHER PUBLICATIONS

Fournier, T. et al.: "Femtosecond laser studies of excited state intramolecular proton transfer in an ultraviolet—filter molecule"; Chem. Phys. Lett. 2000, 325 (1,2,3), 171–175 (Eng), Elsevier Science B.V.; CA Selects: Siloxanes & Silicones, Issue 23, 2000.

Huneke, James T. et al.: "Die Attach Adhesion on Leadframes Treated with Antioxidents"; Oct. 1997 IEEE/CPMT Electronic Packaging Technology Conf.–Singapore.

Ostrauskaite, Jolita et al.: "Synthesis and cationic polymerization of 5–(2,3–epoxypropyl)amino–2–phenyl–1,2,3–benzotriazole"; European Polymer Journal 36 (2000) 2499–2504; Kaunas Univ. of Tech., Kaunas, Lithuania.

Kim, Taek Hyeon et al.: "Melt Free–Radical Grafting of Hindered Phenol Antioxidant onto Polyethylene"; Journal of Applied Polymer Science, vol. 77, 2968–2973 (2000); Kwangju, Korea; John Wiley & Sons, Inc. Pub.

Kim, Taek Hyeon et al.: "Free Radicals Grafting of Hindered Phenol Antioxidents Onto Low Molecular Weight PE"; Polymer Preprints 2000, 41(2), 1237; Kwangju, Korea.

Bartus, Jan et al.: "Functional Polymers. 63.* Emulsion Copolymerization of Maleimide Type Monomers With Acrylonitrile And Styrene in ABS Latexes"; J.M.S.–Pure Appl. Chem., A36(3), pp. 355–371 (1999); 1999 by Marcel Dekker, Inc.

Stoeber, Lutz et al.: "Functional Polymers. 64. Potassium Ionization Of Desorbed Species (K+IDS) Of 2(2–Hydroxyphenyl)2H–Benzotriazoles"; J.M.S.–Pure Appl. Chem., A37(11), pp. 1269–1300 (2000); 2000 by Marcel Dekker, Inc.

Stoeber, Lutz et al.: "Functional Polymers 65. Synthesis And Brief Characterization of Surface Active 2(2–Hydroxyphenyl)2H–Benzotriazole Ultraviolet Stabilizers"; J.M.S.–Pure Appl. Chem., A37(9), pp. 943–970 ; 2000 by Marcel Dekker, Inc.

No Author: Graphs: "A Benzotriazole Family"; "p–Polyhydroxystyrene Family "; TriQuest, LP.

ACS Registry Database Structure Search, 54 Entries, 66 pages.

Kim, H. et al.: "Corrosion protection and adhesion promotion for polyimide/copper system using silane–modified polymeric materials"; Polymer 41 (2000) 6553–6561, Seoul South Korea.

Yu, J. et al.: "Miscibility of Polyimide with Polymeric Primer and Its Influence on Adhesion of Polyimide to the Primed Copper Metal: Effect of Precursor Origin"; Journal of Polymer Science: Part B: Polymer Physics, vol. 37, 2806–2814 (1999); Pub. John Wiley & Sons, Inc.

Ishida, H. et al.: "Modified Imidazoles: Degradation Inhibitors and Adhesion Promoters for Polyimide Films on Copper Substrates"; J. Adhesion, 1991, vol. 36, pp. 177–191; 1991 Gordon and Breach Science Publishers S.A., U.K.

Parthasarathi, Arvind et al.: "Leadframe Treatment To Prevent Delamination In Plastic Packages"; Pub. # 14–115; 1994, 1998 Rogers Corporation.

Dai, Qinpin et al.: "SERS and IR Studies of Polymerization of an Epoxy Compound on Top of Benzotriazole Adsorbed on Copper"; Spectroscopy Letter, 28(1), 43–54 (1995); Marcel Dekker, Inc. 1995.

Xue, Gi et al.: "Stable SERS Substrates Used for In Situ Studies of the Polymer–Metal Interface at Elevated Temperature"; Macromolecules 1994, 27, 809–813; 1994 American Chemical Society.

Poling, G.W.: "Reflection Infra–Red Studies Of Films Formed By Benzotriazole On Cu*"; Corrosion Science, 1970, vol. 10, pp. 359 to 370, Pergamon Press, Printed in Great Britain.

Xue, Gi et al.: "SERS, XPS, and Electroanalytical Studies of the Chemisorption of Benzotriazole on a Freshly Etched Surface and and an Oxidized Surface of Copper"; J. Phys. Chem. 1991, 95, 7380–7384.

Yoshida, Shuji et al.: "A FT–IR Reflection–Adsorption Spectroscopic Study of an Epoxy Coating on Imidazole–Treated Copper"; J. Adhesion, 1984, vol. 16, pp. 217–232; 1984 Gordon & Breach Science Publishers, Inc., U.K.

Mansfield, Florian et al.: Technical Note "Benzotriazole as Corrosion Inhibitor for Copper II. Acid NaCl Solutions"; Corrosion–Nace, North American Rockwell Science Center, Thousand Oaks, CA; Submitted for publication Aug. 1972.

Vogt, Jurgen: "Thermoset Matrices for Structural Adhesives: Imidazole–Catalysed Curing of Epoxy Resins"; J. Adhesion, 1987. vol. 22, pp. 139–151, 1987 Gordon & Breach Science Publishers, Inc., U.K.

Cho, Kilwon et al.: "Effect of the microstructure of copper oxide on the adhesion behavior of epoxy/copper leadframe joints"; J. Adhesion Sci. Technol, vol. 14, No. 11, pp. 1333–1353 (2000).

Lee, H. Y.: "Failure paths of the Cu–based leadframe/EMC joints"; Materials Science and Engineering A311 (2001) 217–225, 2001 Elsevier Science B.V.

Chong, Chai Tai et al.: "Investigation on the Effect of Copper Leadframe Oxidation on Package Delamination"; 1995 IEEE.

Huang, Yizhe Elisa et al.: "Effect Of Solder Reflow Temperature Profile On Plastic Package Delamination"; 1998 IEEE/CPMT Int'l Electronics Manufacturing Technology Symposium.

Kang, Teck–Gyu et al.: "Characterization of Oxidized Copper Leadframes and Copper/Epoxy Molding Compound Interface Adhesion in Plastic Package"; 1998 IEEE.

Schmidt, R. et al.: "Investigation of the Adhesion Strength between Molding Compound and Leadframe at Higher Temperatures"; 1998 IEEE/CPMT Electronics Packaging Technology Conference.

Gaillard, F. et al.: "Grazing–angle Micro–FTIR Spectroscopy (GAM–FTIR): Applications to Adhesion STudies"; Surf. Interface Anal. 27, 865–870 (1999); John Wiley & Sons, Ltd.

Alpern, P. et al.: "A simple model for the mode 1 popcorn effect for IC packages"; Microelectronics Reliability 40 (2000) 1503–1508; 2000 Elsevier Science Ltd. All rights reserved.

Yu, Shan–Pu et al.: "The Adhesion Strength of A Lead–Free Solder Hot–Dipped on Copper Substrate"; Journal of Electronic Materials, vol. 29, No. 2, 2000.

H. Debontride et al.: "Study of Chromating layers on zinc coated steel using FTIR and Raman spectroscopies: application to adhesion properties"; La Revue de Metallurgie–CIT Science et Genie des Materiaux, Mar. 1995.

Gantrez #ES Monoester Resin VVM 8/4/6.76, Nov. 1985.

* cited by examiner

ADHESION PROMOTERS CONTAINING BENZOTRIAZOLES

FIELD OF THE INVENTION

This invention relates to adhesion promoters containing benzotriazole compounds.

BACKGROUND OF THE INVENTION

In the fabrication and assembly of semiconductor packages, an integrated circuit chip or die is attached to a lead frame with adhesive and wire bonding and the die and inner lead frame assembly encapsulated in a molding resin. After encapsulation, the outer leads of the lead frame are attached to a printed circuit board or other external device. Any exposed copper surfaces on lead frames or printed wire boards are subject to oxidation with exposure to air and are routinely coated with antioxidants. Benzotriazole (BTA) is an efficient antioxidant and corrosion inhibitor for copper and copper alloys in many environments, including lead frames and printed wire boards. However, the presence of BTA is suspected of interfering with the bonding process during the die attach, wire bonding, encapsulation, and final soldering operations in the manufacture of the semiconductor package and its attachment to a printed circuit board.

SUMMARY OF THE INVENTION

This invention is a benzotriazole adduct that will contain two chemistry segments: (1) a 2-(2-hydroxyphenyl)benzotriazole segment, which may contain additional hydroxyl groups in the 3, 4, 5, or 6 position of the 2-hydroxyphenyl ring, and (2) a segment that contains electron donor, electron acceptor, epoxy, or acetyl acetonate functionality.

The benzotriazole segment will act as an antioxidant as well as adhesion promoter on metal surfaces. The electron donor, electron acceptor, or epoxy functionality segment will react with adhesive, coating, encapsulant, or other polymerizable compositions to immobilize the benzotriazole and prevent it from interfering with manufacturing operations that are conducted proximate to metal surfaces. The acetyl acetonate functionality will act as an adhesion promoter to metal surfaces.

The electron donor, electron acceptor, epoxy or acetyl acetonate functionality can be attached to the benzotriazole segment through the 2-hydroxyphenyl ring, through the 2-hydroxyl group itself, or through the benzyl ring of the benzotriazole.

In addition to the electron donor, electron acceptor, epoxy, or acetyl acetonate functionality, the 2-hydroxyphenyl ring may also contain a second organic moiety having a reactive functionality.

The benzotriazole adduct may be coated on exposed metal surfaces, such as the copper surfaces of a semiconductor device or printed circuit board, or may be added to adhesive, coating, encapsulant, or other curable compositions that come into contact with or are required to bond to metal surfaces.

DETAILED DESCRIPTION OF THE INVENTION

In one embodiment, the benzotriazole adduct will have the structure:

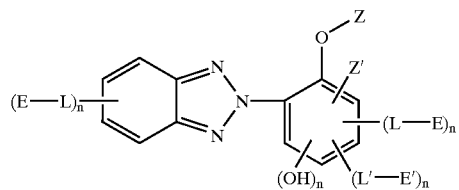

in which n is 0, 1, 2, or 3; E and E' independently are an organic moiety containing electron donor, epoxy, acetyl acetonate, or electron acceptor excluding acrylate, functionality; Z is hydrogen, hydrocarbyl, or an organic moiety containing electron donor, epoxy, acetyl acetonate, or electron acceptor excluding acrylate, functionality; Z' is hydrogen, hydrocarbyl, an electron donating group (such as, —OCH$_3$, phenyl); an electron withdrawing group (such as —NO$_2$, —CN); and L and L' independently are a direct bond, a hydrocarbyl group, or a functionality selected from the group consisting of

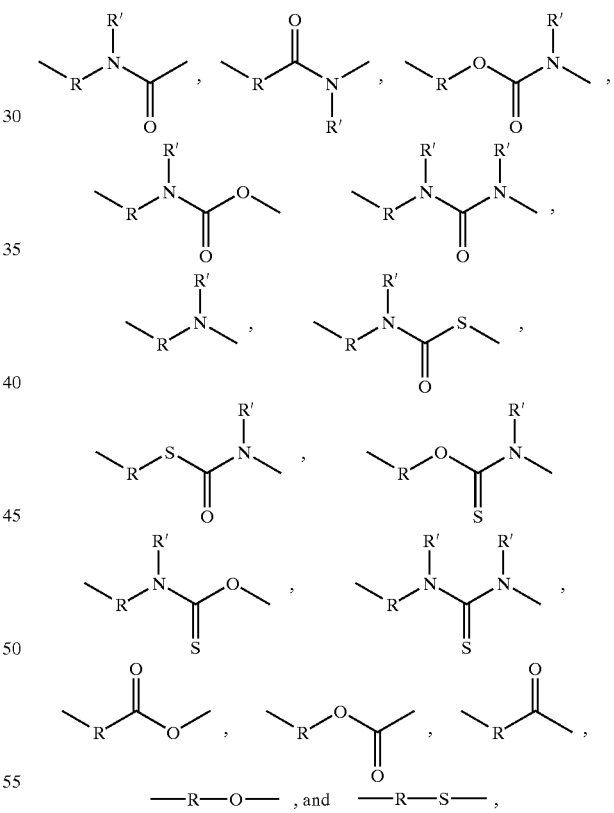

in which R is a direct bond or a hydrocarbyl group attached to the benzotriazole segment, and R' is hydrogen, an aromatic, or an alkyl group of 1 to 6 carbon atoms, and preferably is hydrogen, methyl or ethyl.

Provided: that if n is 0 for each of (E-L), (L-E), or (L'-E'), then Z is not hydrogen or alkyl; and if L or L' is a direct bond, or if L or L' is alkyl and E is a maleimide or a styrene group, then for (L-E) or (L'-E'), n must be more than 1, or for (E-L), n must be at least one.

Within this specification and claims, hydrocarbyl group means, for example, a linear or branched alkyl or alkenyl group or a cyclic alkyl or alkenyl group, or an aromatic group. An organic moiety containing an electron donor, electron acceptor, epoxy, vinyl, or acetyl acetonate functionality, means that functionality itself, or that functionality with a hydrocarbyl group.

Exemplary electron donor groups are vinyl ethers, vinyl silanes, compounds containing carbon to carbon double bonds attached to an aromatic ring and conjugated with the unsaturation in the aromatic ring, such as compounds derived from cinnamyl and styrenic starting compounds. Exemplary electron acceptor groups are fumarates, maleates, and maleimides; specifically excluded are acrylates.

In another embodiment the benzotriazole adduct will have the structure:

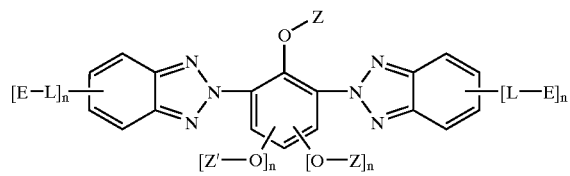

in which n, E, L, Z and Z' are as described above and at least one of Z and Z' cannot be hydrogen or alkyl.

The benzotriazole adduct compounds of this invention, and other benzotriazole adducts having polymerizable segments positioned as the E, E', Z or Z' groups in the above structures, can be used as curable compositions, or as additives to retard oxidation and promote adhesion in curable compositions, such as in adhesive, coating and encapsulant formulations, particularly those used proximate to metal substrates. Such other polymerizable segments include acrylates and methacrylates, vinyl groups, (meth) acryl amino groups, glycidyl groups, and siloxanes. (See, for example, U.S. Pat. Nos. 3,493,539, 3,399,173, 4,428,987, 4,448,847, 5,627,227, and EP patent applications 0285266A2, 0251490A2, and 1,033,590A2).

In such cases, the amount used in a formulation will be an effective amount to promote antioxidative results and adhesion. In general, an effective amount will range from 0.005 to 20.0 percent by weight of the adhesive, coating, or encapsulant formulation. In addition, such formulations will contain a curable resin, optionally a curing initiator, and optionally a conductive or nonconductive filler.

Suitable curable resins that may be used in the adhesive, coating, encapsulant or sealant formulations are known to practitioners in those arts. Examples of such resins include epoxies, electron donor resins (for example, vinyl ethers, vinyl silanes, thiol-enes, and resins that contain carbon to carbon double bonds attached to an aromatic ring and conjugated with the unsaturation in the aromatic ring, such as compounds derived from cinnamyl and styrenic starting compounds), and, electron acceptor resins (for example, fumarates, maleates, acrylates, and maleimides).

Suitable curing agents are thermal initiators and photoinitiators present in an effective amount to cure the adhesive, coating, encapsulant or sealant formulation. In general, those amounts will range from 0.5% to 30%, preferably 1% to 20%, by weight of the total organic material (that is, excluding any inorganic fillers) in the formulation. Preferred thermal initiators include peroxides, such as butyl peroctoates and dicumyl peroxide, and azo compounds, such as 2,2'-azobis(2-methyl-propanenitrile) and 2,2'-azobis(2-methyl-butanenitrile). A preferred series of photoinitiators is one sold under the trademark Irgacure by Ciba Specialty Chemicals. In some formulations, both thermal initiation and photoinitiation may be desirable: the curing process can be started either by irradiation, followed by heat, or can be started by heat, followed by irradiation.

In general, the formulations will cure within a temperature range of 70° C. to 250° C., and curing will be effected within a range of ten seconds to three hours. The actual cure profile will vary with the components and can be determined without undue experimentation by the practitioner.

The formulations may also comprise electrically or thermally conductive fillers or nonconductive fillers. Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. If present, fillers generally will be in amounts of 20% to 90% by weight of the formulation.

In another embodiment, the benzotriazole adducts of this invention can be used to coat exposed metal surfaces, and in particular, copper surfaces. (The metal surface may first be degreased, cleaned, polished or buffed.) In this embodiment, the benzotriazole adduct typically is used at a concentration of 0.5% to 20% in any suitable solvent. Representative suitable solvents are water, ketones (such as, methyl ethyl ketone, methyl isobutyl ketone, acetone), alcohols, glycol ethers, esters, and toluene. The metal substrate is immersed in the solution for a period of time sufficient to deposit an effective coating. Immersion times typically will range from one second to one hour, more typically one minute to 15 minutes, although shorter or longer times may be effective depending on the particular benzotriazole compound, solution strength, and solution temperature. In general, the solution bath will be at a temperature within the range of 15° C. to 100° C. Alternatively, the benzotriazole compound in solution can be sprayed or painted onto the metal surface to be coated. The solution is typically air-dried from the surface, and then cured at an elevated temperature suitable for removing any remaining solvent and for effecting curing.

Figure 1:
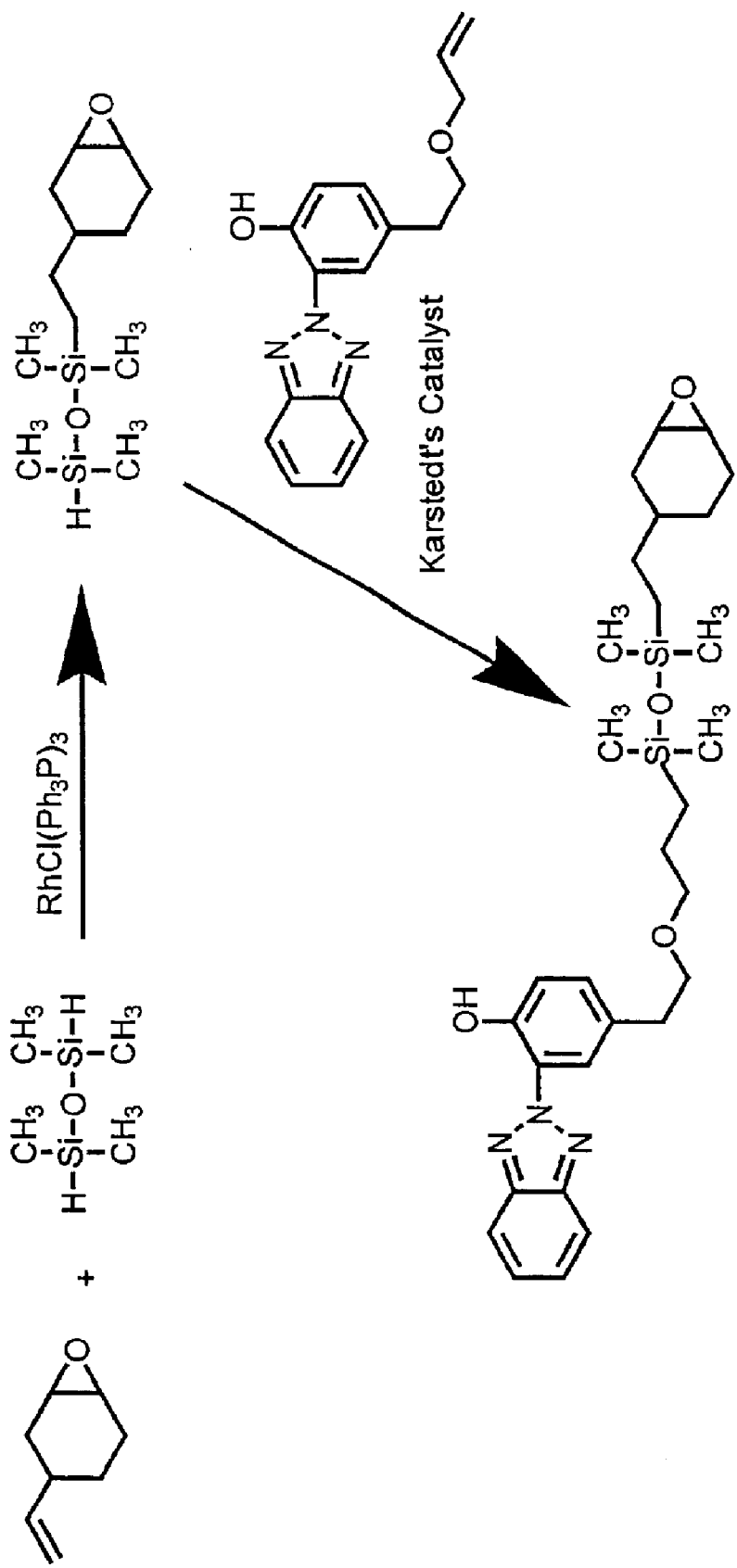
FIG. 1 is a benzotriazole adduct prepared according Example 21.

The following are the Synthetic Procedures used to make the benzotriazole adducts disclosed in this specification, examples of benzotriazole adducts and performance.

SYNTHETIC PROCEDURES

PROCEDURE 1. Reaction of isocyanate with alcohol. One mole equivalent of isocyanate is solvated in toluene in a three-necked flask equipped with a mechanical stirrer, addition funnel and nitrogen inlet/outlet. The reaction is placed under nitrogen and catalytic of dibutyltin dilaurate is added with stirring as the solution is heated to 60° C. The addition funnel is charged with one mole equivalent of alcohol dissolved in toluene. This solution is added to the isocyanate solution over ten minutes, and the resulting mixture is heated for an additional three hours at 60° C. After the reaction is allowed to cool to room temperature, the solvent is removed in vacuo to give the product.

PROCEDURE 2. Reaction of isocyanate with amine. One mole equivalent of isocyanate is solvated in toluene in a three-necked flask equipped with a mechanical stirrer, addition funnel and nitrogen inlet/outlet. The reaction is placed under nitrogen and the solution heated to 60° C. The addition funnel is charged with one mole equivalent of amine in toluene, and this solution is added to the isocyanate solution over ten minutes. The resulting mixture is heated for an additional three hours at 60° C., after which it is allowed to cool to room temperature. The solvent is removed in vacuo to give the product.

PROCEDURE 3. Reaction of alkyl halide with amine or mercaptan. One mole equivalent of alkyl halide is solvated in THF in a three neck flask equipped with a mechanical stirrer and addition funnel. The addition funnel is charged with one mole equivalent of amine or mercaptan in THF and this solution is added to the alkyl halide solution over ten minutes at 0° C. The resulting mixture is stirred for 12 hours at room temperature, after which the solvent is removed in vacuo and ether and water are added to the resulting material. The organic layer is extracted and dried over $MgSO_4$, and the solvent removed in vacuo to give the product.

PROCEDURE 4. Reaction of alkyl halide with alcohol. One mole equivalent of alcohol, an excess amount of 50% NaOH, a catalytic amount of tetrabutyl ammonium hydrogen sulfate, and one mole equivalent of alkyl halide in toluene are stirred for five hours at 53° C., then for five hours at 75° C. The reaction is allowed to cool to room temperature and the organic layer extracted and washed with brine three times. The isolated organic layer is dried over $MgSO_4$, filtered, and the solvent removed in vacuo to give the product.

PROCEDURE 5. Conversion of alcohol functionality to chloride functionality. The synthetic procedure is conducted according to E. W. Collington and A. I. Meyers, *J. Org. Chem.* 36, 3044 (1971). To a stirred mixture of one mole equivalent of alcohol and 1.1 mole equivalent of s-collidine under nitrogen is added one equivalent of lithium chloride dissolved in a minimum amount of dry dimethylformamide. On cooling to 0° C., a suspension is formed and this is treated dropwise with 1.1 mole equivalent of methanesulfonyl chloride. Stirring is continued at 0° C. for one to one and one-half hour, after which the pale yellow reaction mixture is poured over ice-water. The aqueous layer is extracted with cold ether/pentane (1:1) and the combined extracts are washed successively with saturated copper nitrate solution. This is continued until no further intensification of the blue copper solution occurs, indicating complete removal of s-collidine. The organic extracts are dried over $Na_2SO_4$ and concentrated at room temperature, providing the product.

PROCEDURE 6. Reaction of amine with acid chloride. One equivalent of amine and one equivalent of triethylamine are mixed in dry methylene chloride at 0° C. One equivalent of acid chloride dissolved in dry methylene chloride is added and the mixture allowed to react for four hours. The solvent is evaporated and the crude product is purified by column chromatography using a gradient of hexane/ethyl acetate to give the product.

PROCEDURE 7. Reaction of alcohol with acid chloride. One mole equivalent of alcohol and of triethylamine are mixed in dry methylene chloride at 0° C. One mole equivalent acid chloride dissolved in dry methylene chloride is added and the mixture allowed to react for four hours. The solvent is evaporated and the crude product is purified by column chromatography using a gradient of hexane/ethyl acetate to give the product.

PROCEDURE 8. Reaction of alcohol with carboxylic acid. One mole equivalent of carboxylic acid, one mole equivalent of alcohol, and a catalytic amount of sulfuric acid are solvated with toluene in a four-necked flask fitted with a Dean Stark apparatus, mercury thermometer, mechanical stirrer, and an inlet/outlet tube. The reaction mixture is blanketed with nitrogen and the temperature raised to reflux (110° C.). Reflux is maintained for approximately four hours, at which point water (indicating the reaction is progressing) is obtained in the Dean Stark trap along with solvent. The condensate trap is emptied to remove the collected water and toluene and an amount of toluene equal to the amount of water and toluene removed is charged to the flask to maintain a consistent solvent level. Following another 30 minutes of reflux, the trap is again emptied and the reaction flask recharged with fresh solvent to replace the distillate that is removed. This process is repeated four more times to maximize water removal from the system. Following the final 30 minutes of reflux, the heat is removed, the solvent is evaporated, and the crude product is purified by column chromatography using a gradient of hexane/ethyl acetate to give the product.

PROCEDURE 9. Reaction of alcohol with vinyl silane. One mole equivalent of alcohol and triethylamine are mixed in dry toluene at 0° C., to which is added one mole equivalent of vinyl silane dissolved in toluene. The mixture is allowed to react for four hours at room temperature, after which the solvent is evaporated to give the product.

PROCEDURE 10. Reaction of isocyanate with mercaptan. One mole equivalent of isocyanate is solvated in toluene in a three-necked flask equipped with a mechanical stirrer, addition funnel and nitrogen inlet/outlet. The reaction is placed under nitrogen and the solution heated to 60° C. The addition funnel is charged with one mole equivalent of mercaptan in toluene. This solution is added to the isocyanate solution over ten minutes, and the resulting mixture is heated for an additional three hours at 60° C. After the reaction is allowed to cool to room temperature, the solvent is removed in vacuo to give the product.

PROCEDURE 11. Reaction of isothiocyanate with alcohol. One mole equivalent of isothiocyanate is solvated in toluene in a three-necked flask equipped with a mechanical stirrer, addition funnel and nitrogen inlet/outlet. The reaction is placed under nitrogen, and a catalytic amount of dibutyltin dilaurate is added with stirring as the solution is heated to 60° C. The addition funnel is charged with one mole equivalent of alcohol dissolved in toluene, which is added to the isothiocyanate solution over ten minutes. The resulting mixture is heated for an additional three hours at 60° C. After the reaction is allowed to cool to room temperature, the solvent is removed in vacuo to give the product.

PROCEDURE 12. Hydrosilation. A solution of one mole equivalent of alkene and toluene is prepared, to which is added with stirring a catalytic amount of hydrogen hexachloroplatinate (IV) hydrate ($H_2PtCl_6$, available from Adrich). The resulting solution is heated to 80° C. and one mole equivalent of silicon hydride is added gradually via a syringe. The resulting mixture is heated for an additional one hour at 80° C. and the reaction is allowed to cool to room temperature. The solvent is removed in vacuo to give the product.

PROCEDURE 13. Reaction of carboxylic acid with isocyanate. The synthesis is conducted according to T. Nishikubo, E. Takehara, and A. Kameyama, *Polymer Journal*, 25, 421 (1993). A stirred mixture of one mole equivalent of isocyanate and one mole equivalent of carboxylic acid is solvated in toluene in a three-necked flask equipped with a mechanical stirrer and nitrogen inlet/outlet. The mixture is heated for two hours at 80° C., and then allowed to cool to room temperature. The solvent removed in vacuo to give the product.

PROCEDURE 14. Reaction of disiloxane with vinyl epoxy. A round-bottomed flask is charged with one mole equivalent of disiloxane and one mole equivalent of vinyl epoxy resin. The reaction flask is equipped with a magnetic stirrer and a reflux condenser. To this mixture is added a catalytic amount of tris(triphenylphosphine)rhodium(l) chloride, and the reaction mixture is heated to 80–85° C. for six hours. The reaction is followed using gas chromatography by monitoring the disappearance of the starting materials and the appearance of the products. After the completion of the reaction, pure product is obtained by fractional vacuum distillation.

PROCEDURE 15. Synthesis of epoxy functional benzotriazole. One mole equivalent of benzotriazole is dissolved in toluene and placed in a two-necked round bottomed flask. One mole equivalent of epoxy siloxane adduct is added to the flask, and the reaction mixture is heated to 60° C. One drop of Karstedt's catalyst is added to initiate the hydrosilation reaction, which is monitored by following the disappearance of Si—H band at 2117 $cm^{-1}$ in the infrared spectrum. The reaction is over in approximately two to three hours. After cooling, the reaction mixture is poured with stirring into methanol to precipitate the product. The precipitated benzotriazole is washed with methanol and dried in vacuo at 60° C. for eight hours.

PROCEDURE 16. Reaction of phenol or acetoacetate with alkyl or alkenyl halide. One mole equivalent of phenol or acetoacetate is charged to a three-necked flask equipped with a mechanical stirrer, condenser, and inlet/outlet tube for nitrogen. Methyl ethyl ketone is added and the reaction placed under nitrogen gas. Alkyl or alkenyl halide is added through a syringe and stirring initiated. Potassium carbonate is added and the reaction mixture heated at 50° C. for 11 hours, allowed to cool to room temperature, and vacuum filtered. The filtrate is washed with 5% NaOH and 10% $Na_2SO_4$. The organic layer is dried over $MgSO_4$, and the solvent evaporated off to give the product.

PROCEDURE 17. Reaction of alcohol or amine with diketene. Alcohol or amine, and acetone and triethylamine are added to a three-necked flask equipped with an addition funnel and magnetic stirrer. The mixture is cooled to 0° C. and diketene in acetone is added to the addition funnel under nitrogen. Diketene is added to the flask over approximately 30 minutes, after which the reaction mixture is stirred at room temperature for five hours. The solvent is removed under reduced pressure and the solid product is ground with mortar and pestle and washed with water in a beaker. The mixture is vacuum filtered and the solid is washed with hexane. This product is placed in an aluminum pan and dried in a vacuum oven to give the product.

PROCEDURE 18. Reaction of phenol with epoxy. An agitated mixture of one mole equivalent of epoxy resin, one mole equivalent of phenolic resin, and 0.4 mole equivalent of tetramethylammonium chloride is heated to 85° C., and maintained at this temperature for a period of 12 hours. Upon being cooled to room temperature, the resulting reaction product partially solidified. The resulting material is recrystallized from methanol-water solution to give the product.

PROCEDURE 19. Reaction of carboxylic acid with epoxy. An agitated mixture of one mole equivalent of epoxy resin, one mole equivalent of carboxylic acid resin, and 0.4 mole equivalent of tetramethylammonium bromide is heated to 80° C., and maintained at this temperature for a period of 10 hours. Upon being cooled to room temperature, the resulting reaction product, which is in the form of a viscous oil, is removed and subjected to a base titration. The resulting material is recrystallized from methanol-water solution to give the product.

PROCEDURE 20. Reaction of benzotriazole with alcohol. In a round-bottle flask, one mole equivalent of benzotriazole and one mole equivalent of alcohol are dissloved in 97% sulfuric acid and stirred using a Teflon-coated magnetic stirring bar during 20 hours. The flask is cooled with ice for the first two hours, after which the solution is allowed to come to room temperature. At the end of the reaction, the solution is poured into ice and water to precipitate the product. The suspension is filtered, and the collected crude product washed with water and dried. The crude product is recrystallized from a 1:1 mixture of ethanol-ethyl acetate.

EXAMPLES

Example 1

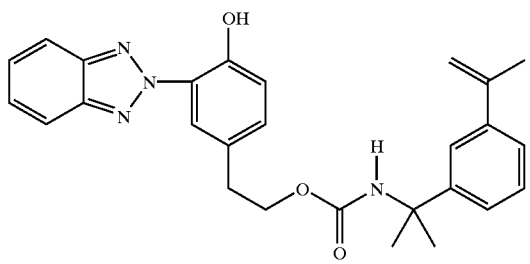

3-Isopropenyl-α,α-dimethylbenzyl isocyanate (m-TMI, 30.0g, 0.149 mole) was solvated in 50 mL toluene in a 500 mL three-necked flask equipped with a mechanical stirrer, addition funnel and nitrogen inlet/outlet. The reaction was placed under nitrogen, and 0.01 equivalent catalytic dibutyltin dilaurate was added with stirring as the solution heated to 70° C. The addition funnel was charged with 3-(2H-benzotriazole-2-yl)-4-hydroxyphenethyl alcohol (38.1 g, 0.149 mole) dissolved in 50 mL toluene and this was added to the isocyanate solution over ten minutes. The resulting mixture was heated for an additional three hours at 70° C. After the reaction was allowed to cool to room temperature, the mixture was washed with distilled water three times. The isolated organic layer was dried over $MgSO_4$, filtered, and the solvent removed in vacuo to give the product in 97% yield.

Example 2

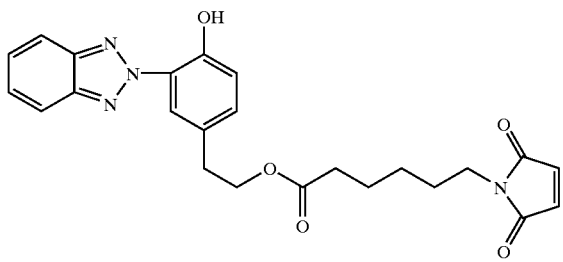

A solution of one mole equivalent of maleic anhydride in acetonitrile was added to a one mole equivalent of 6-aminocaprioc acid in acetic acid. The mixture was allowed to react for three hours at room temperature. The formed white crystals were filtered off, washed with cold acetonitrile and dried to produce the amic acid adduct. The amic acid adduct was mixed with triethylamine in toluene, the mixture heated to 130° C. for two hours and the water of reaction collected in a Dean-Stark trap. The organic solvent was evaporated and 2M HCL added to reach pH 2. The product was extracted with ethyl acetate, and the ethyl acetate solution was dried over $MgSO_4$. The solvent was evaporated to give 6-maleimidocaproic acid (MCA).

6-Maleimidocaproic acid (MCA, 18.17 g, 0.0861 mole), 3-(2H-benzotriazole-2-yl)-4-hydroxyphenethyl alcohol (20.0 g, 0.0783 mole) and 250 mL toluene were added to a 500 mL three-necked flask and heated to 80° C. until solids were dissolved. Sulfuric acid catalyst (0.384 g) was added and the heat was increased to 140° C. After 11 hours of heating, the water of reaction (1.41 mL) and toluene (25 mL) were removed from Dean-Stark apparatus. Fresh toluene (25 mL) was replaced in the flask. This was repeated three times to maximize water removal from the system. Triethyl amine (7.80 mL) was added and the mixture was allowed to stir for one hour at room temperature. NaCl (20%) was added to the mixture and the mixture transfered to a separatory funnel. The organic layer was isolated and dried over $MgSO_4$ followed by evaporation of the solvent to give the product in 75% yield.

Example 3

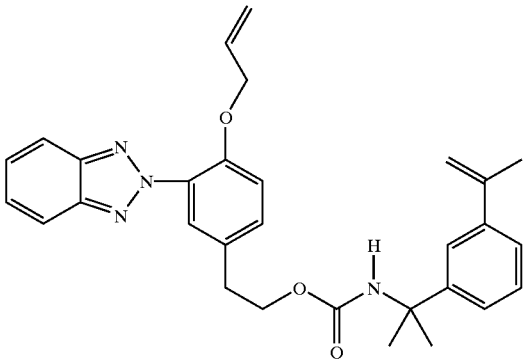

The product from Example 1 (10 g, 0.0219 mole) and 80 mL methyl ethyl ketone were added to a 250 mL three-necked flask equipped with a mechanical stirrer and condenser and placed under nitrogen gas. Allyl bromide (7.95 g, 0.066 mole) was added to the flask through a syringe and stirring was initiated. Potassium carbonate was added to the flask and the reaction mixture was heated at 50° C. for 11 hours, after which it was allowed to cool to room temperature and vacuum filtered. The filtrate was washed with 5% NaOH and 10% $Na_2SO_4$. The organic layer was dried over $MgSO_4$ followed by evaporation of the solvent to give the product in 65% yield.

Example 4

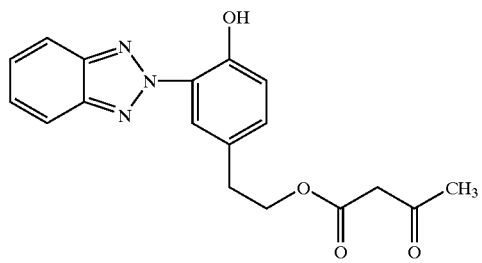

In a 500 mL three-necked flask equipped with an addition funnel and stirrer was added 3-(2H-benzotriazole-2-yl)-4-hydroxyphenethyl alcohol (46.72 g, 0.183 mole), 150 mL reagent grade acetone and triethylamine. The mixture was cooled to 0° C. Diketene (20 g, 0.238 mole) in 20 mL acetone was added to the addition funnel under nitrogen and added to the flask over approximately 30 minutes. The reaction mixture was stirred at room temperature for 5 hours, after which the solvent was removed under reduced pressure. The solid product was ground with mortar and pestle and washed with water in a beaker. The mixture was vacuum filtered and the solid washed with hexane. The product was placed in an aluminum pan and dried in a vacuum oven to give the product in 85% yield.

Example 5

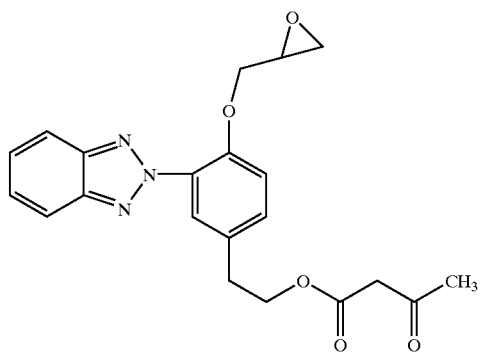

A benzotriazole adduct prepared according to Procedure 16 by the reaction of 3-(2H-benzotriazole-2-yl)-4-hydroxyphenethyl alcohol and epichlorohydrin, followed by reaction with diketene according to Procedure 17.

Example 6

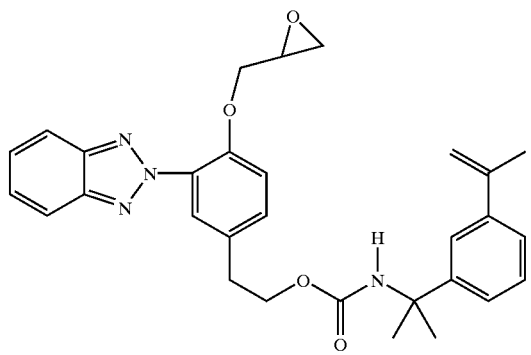

A benzotriazole adduct prepared according to Procedure 16 by the reaction of 3-(2H-benzotriazole-2-yl)-4-hydroxyphenethyl alcohol and epichlorohydrin, followed by reaction with M-TMI according to Procedure 1.

Example 7

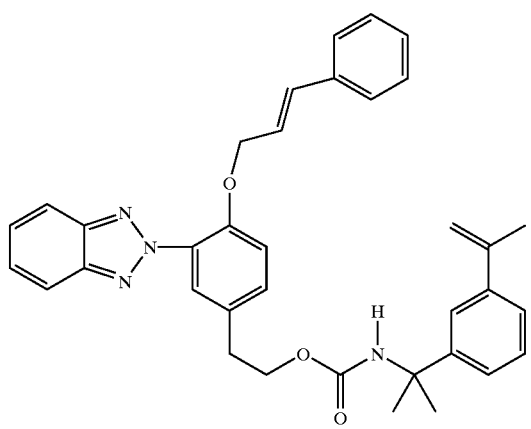

A benzotriazole adduct prepared according to Procedure 16 by the reaction of 3-(2H-benzotriazole-2-yl)-4-hydroxyphenethyl alcohol and cinnamyl chloride, followed by reaction with m-TMI according to Procedure 1.

Example 8

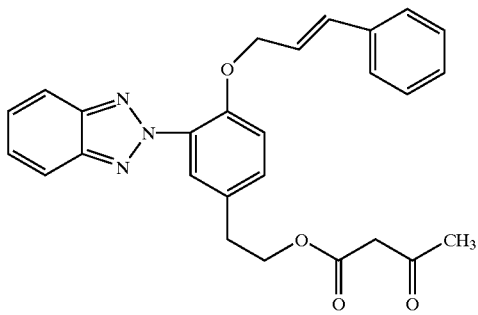

A benzotriazole adduct prepared according to Procedure 16 by the reaction of 3-(2H-benzotriazole-2-yl)-4-hydroxyphenethyl alcohol and cinnamyl chloride, followed by reaction with diketene according to Procedure 17.

Example 9

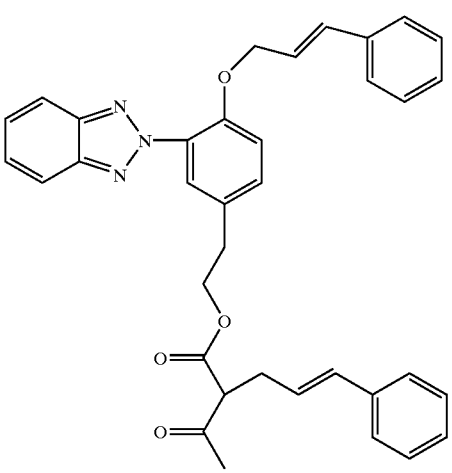

A benzotriazole adduct prepared according to Procedure 16 by the reaction of the product from Example 9 with cinnamyl chloride.

Example 10

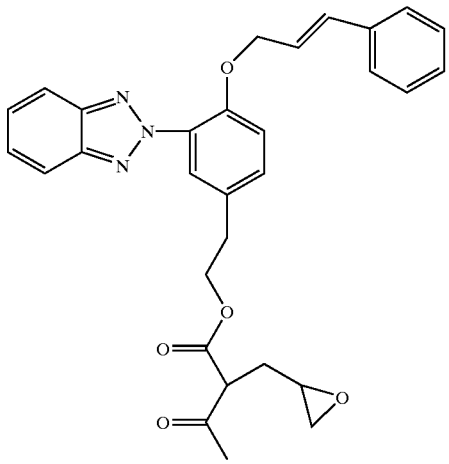

A benzotriazole adduct prepared according to Procedure 16 by the reaction of the product from Example 9 and epichlorohydrin.

Example 11

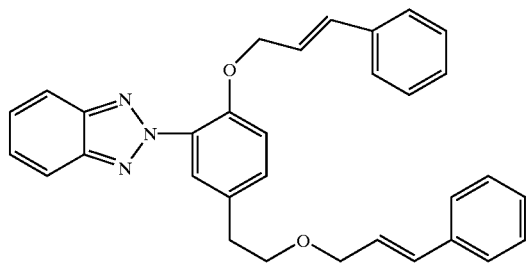

A benzotriazole adduct prepared according to Procedure 16 by the reaction of 3-(2H-benzotriazole-2-yl)-4-hydroxyphenethyl alcohol and cinnamyl chloride, followed by reaction with cinnamyl chloride according to Procedure 4.

Example 12

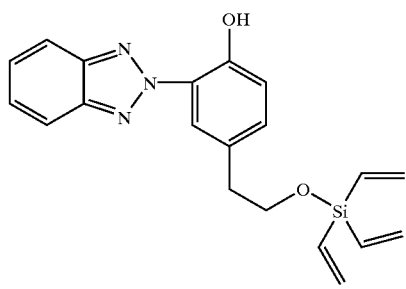

A benzotriazole adduct prepared according to Procedure 9 by the reaction of 3-(2H-benzotriazole-2-yl)-4-hydroxyphenethyl alcohol and trivinyl chlorosilane.

Example 13

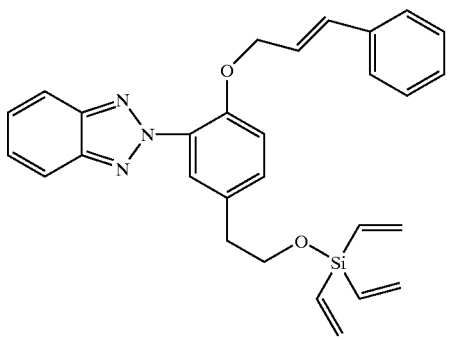

A benzotriazole adduct prepared according to Procedure 16 by the reaction of 3-(2H-benzotriazole-2-yl)-4-hydroxyphenethyl alcohol and cinnamyl chloride, followed by reaction with trivinyl chlorosilane according to Procedure 9.

Example 14

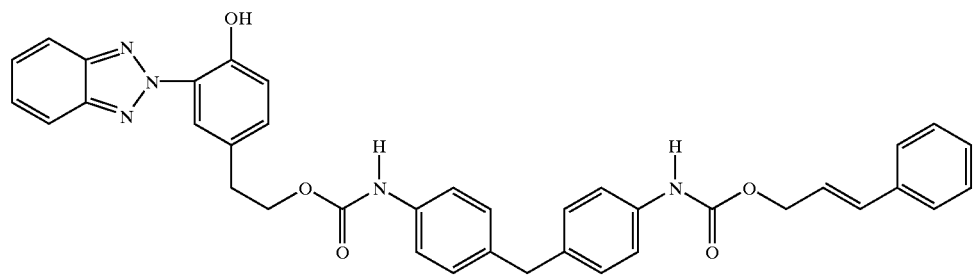

A benzotriazole adduct prepared according to Procedure 1 by the reaction of 3-(2H-benzotriazole-2-yl)-4-hydroxyphenethyl alcohol and 4,4'methylene di(phenylisocyanate) (MDI), followed by reaction with cinnamyl alcohol according to Procedure 1.

Example 15

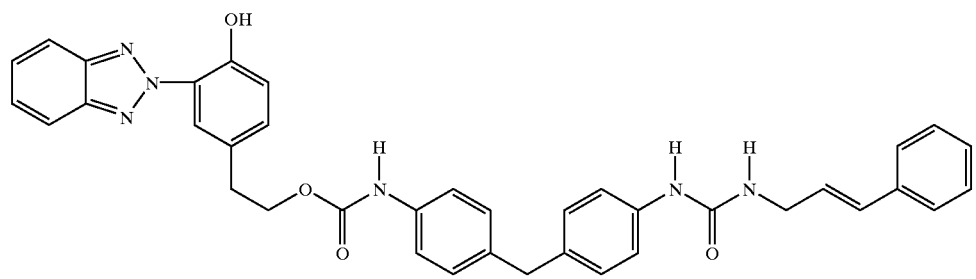

A benzotriazole adduct prepared according to Procedure 1 by the reaction of 3-(2H-benzotriazole-2-yl)-4-hydroxyphenethyl alcohol and 4,4'methylene di(phenylisocyanate) (MDI), followed by reaction with cinnamyl amine according to Procedure 2.

Example 16

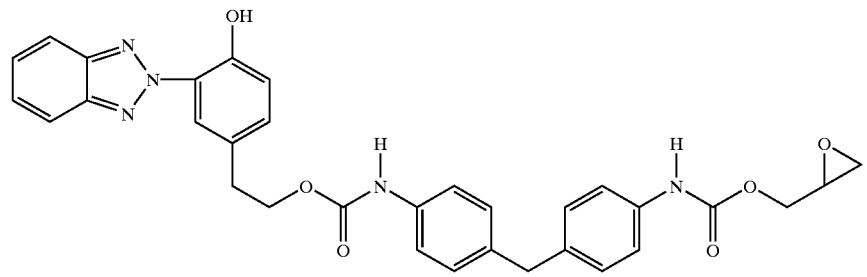

A benzotriazole adduct prepared according to Procedure 1 by the reaction of 3-(2H-benzotriazole-2-yl)-4-hydroxyphenethyl alcohol and 4,4'methylene di(phenylisocyanate) (MDI), followed by reaction with glycidol according to Procedure 1.

Example 17

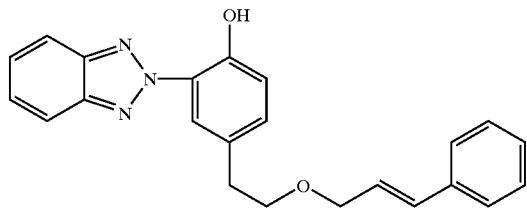

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with cinnamyl alcohol according to Procedure 4.

Example 18

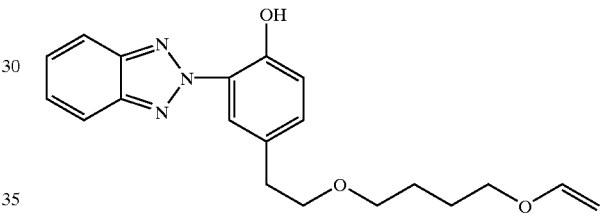

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with hydroxybutyl vinyl ether according to Procedure 4.

Example 19

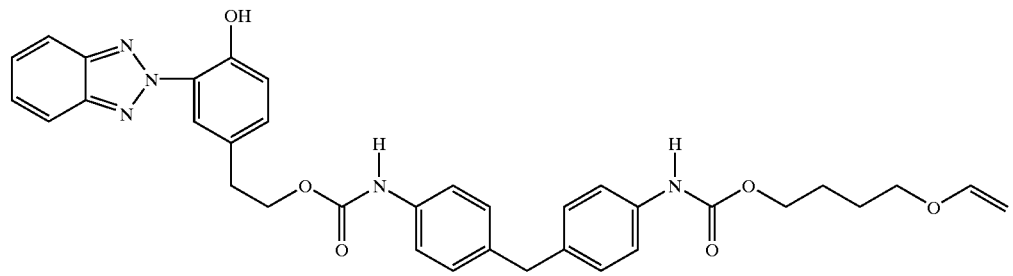

A benzotriazole adduct prepared according to Procedure 1 by the reaction of 3-(2H-benzotriazole-2-yl)-4-hydroxyphenethyl alcohol and 4,4'methylene di(phenylisocyanate) (MDI), followed by reaction with hydroxybutyl vinyl ether according to Procedure 1.

Example 20

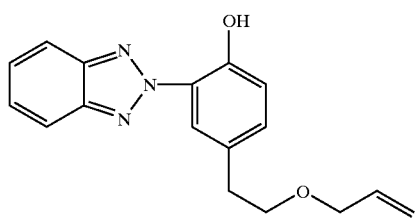

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with allyl alcohol according to Procedure 4.

Example 21

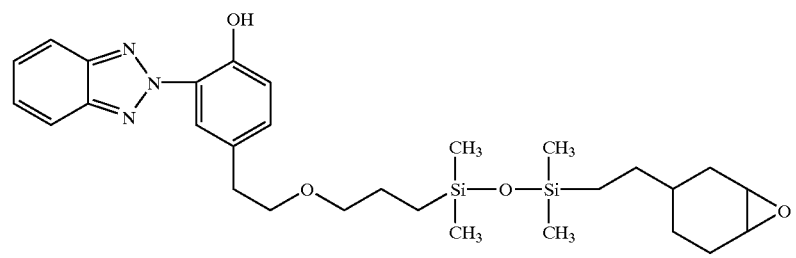

A benzotriazole adduct prepared according to Procedure 14 by the reaction of 3-vinyl-7-oxabicyclo[4.1.0]heptane with 1,1,3,3-tetramethyldisiloxane to give 1-[2-(3[7-oxabicyclo[4.1.0]heptyl])ethyl]-1,1,3,3-tetramethyldisiloxane, then by the reaction of the benzotriazole adduct from Example 23 according to Procedure 15.

Example 22

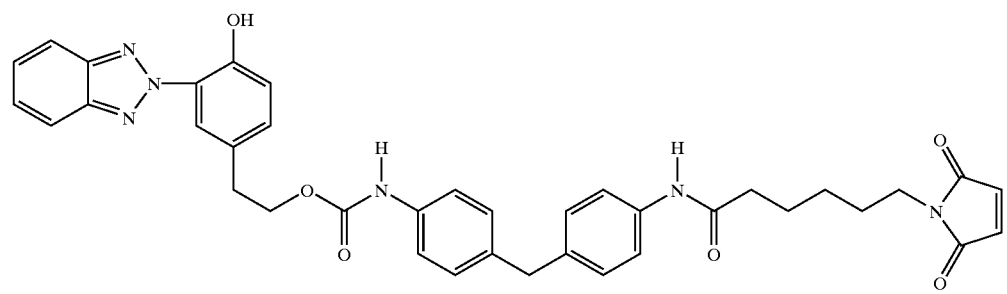

A benzotriazole adduct prepared according to Procedure 1 by the reaction of 3-(2H-benzotriazole-2-yl)-4-hydroxyphenethyl alcohol with 4,4'methylene di(phenylisocyanate) (MDI), followed by reaction with 6-maleimidocaproic acid (synthesis described in Example 2) according to Procedure 13.

Example 23

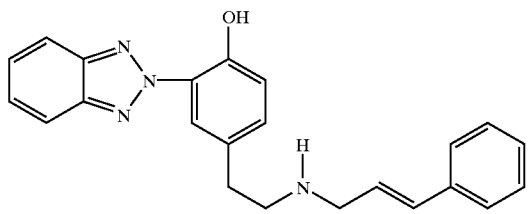

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with ammonia according to Procedure 3. The product, which is a primary amine, is reacted with cinnamyl chloride according to Procedure 3.

Example 24

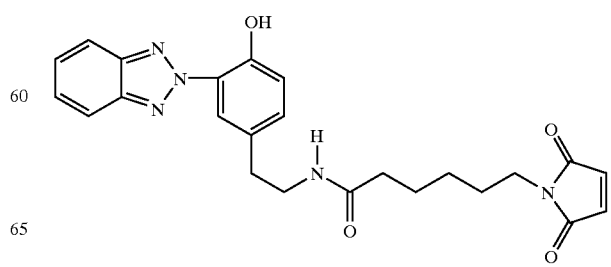

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with ammonia according to Procedure 3. The product, which is a primary amine, is reacted with 6-maleimidocaproic acid chloride (prepared from 6-maleimidocaproic acid and thionyl chloride according to Procedure 6) according to Procedure 3. See FIG. 1.

Example 25

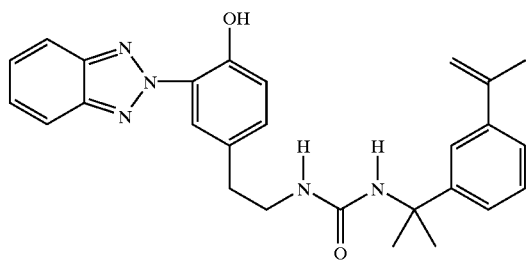

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with ammonia according to Procedure 3. The product, which is a primary amine, is reacted with m-TMI according to Procedure 2.

Example 26

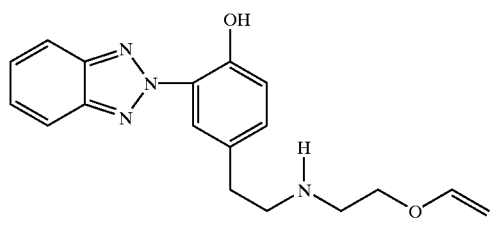

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with ammonia according to Procedure 3. The product, which is a primary amine, is reacted with chloroethyl vinyl ether according to Procedure 3.

Example 27

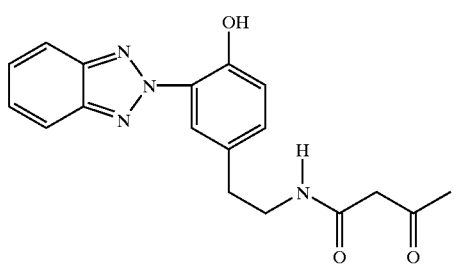

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with ammonia according to Procedure 3. The product, which is a primary amine, is reacted with diketene according to Procedure 17.

Example 28

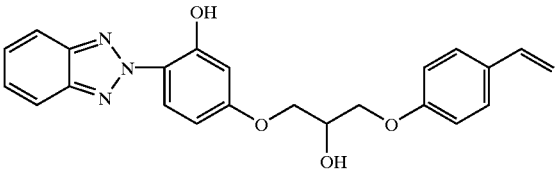

A benzotriazole adduct prepared according to Procedure 18 by the reaction of 2-(2,4-dihydroxyphenyl)benzotriazole with [(4-ethenylphenoxy)methyl]-oxirane.

Example 29

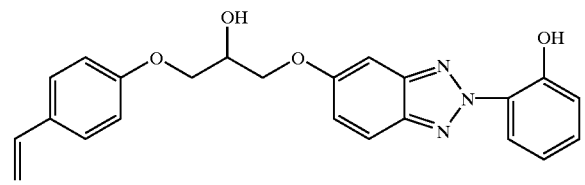

A benzotriazole adduct prepared according to Procedure 18 by the reaction of 5-hydoxy-2-(hydroxyphenyl) benzotriazole with [(4-ethenylphenoxy)methyl]-oxirane.

Example 30

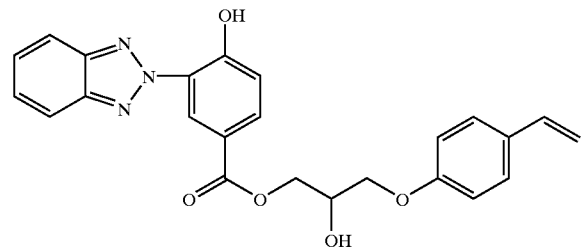

A benzotriazole adduct prepared according to Procedure 19 by the reaction of 2-(5-carboxy-2-hydrophenyl) benzotriazole with [(4-ethenylphenoxy)methyl]-oxirane.

Example 31

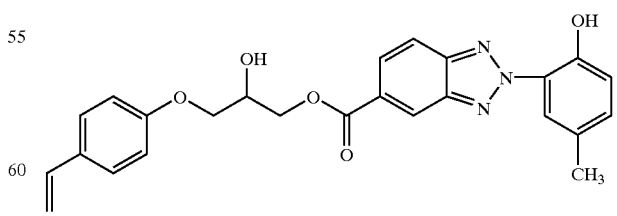

A benzotriazole adduct prepared according to Procedure 19 by the reaction of 5-carboxy-2-(5-methyl-2-hydroxyphenyl) benzotriazole with [(4-ethenylphenoxy)methyl]-oxirane.

Example 32

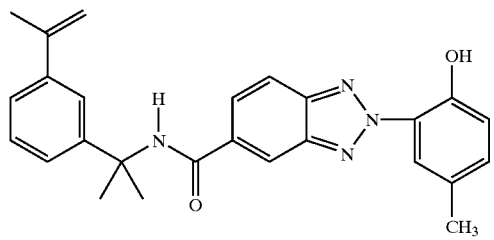

A benzotriazole adduct prepared according to Procedure 13 by the reaction of 5-carboxy-2-(5-methyl-2-hydroxyphenyl) benzotriazole with m-TMI.

Example 33

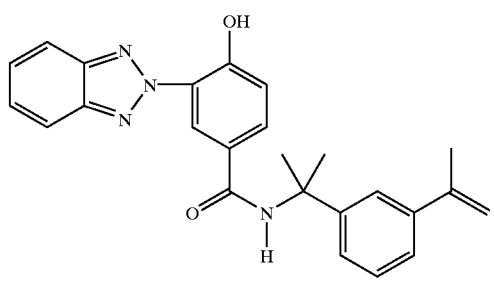

A benzotriazole adduct prepared according to Procedure 13 by the reaction of 2-(5-carboxy-2-hydrophenyl) benzotriazole with m-TMI.

Example 34

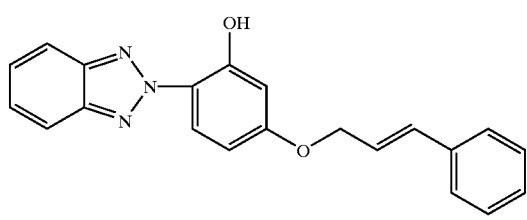

A benzotriazole adduct prepared according to Procedure 16 by the reaction of 2-(2,4-dihydroxyphenyl)benzotriazole with cinnamyl chloride.

Example 35

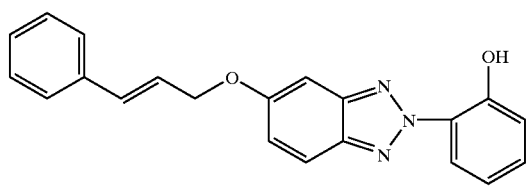

A benzotriazole adduct prepared according to Procedure 16 by the reaction of 5-hydroxy-2-(hydroxyphenyl) benzotriazole with cinnamyl chloride.

Example 36

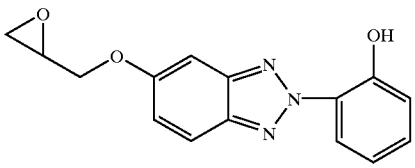

A benzotriazole adduct prepared according to Procedure 16 by the reaction of 5-hydoxy-2-(hydroxyphenyl) benzotriazole with epichlorohydrin.

Example 37

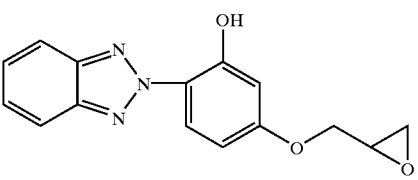

A benzotriazole adduct prepared according to Procedure 16 by the reaction of 2-(2,4-dihydroxyphenyl)benzotriazole with epichlorohydrin.

Example 38

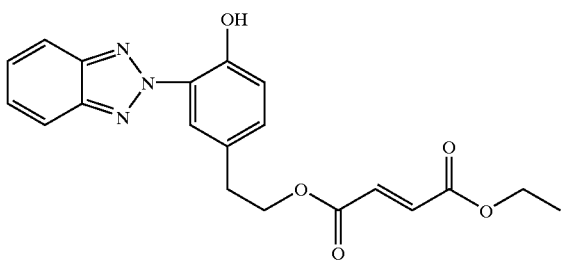

A benzotriazole adduct prepared according to Procedure 8 by the reaction of 3-(2H-benzotriazole-2-yl)-4-hydroxyphenethyl alcohol and fumaric acid ethyl ester.

Example 39

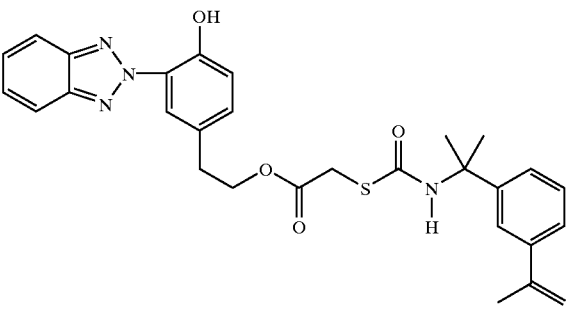

A benzotriazole adduct prepared according to Procedure 8 by the reaction of 3-(2H-benzotriazole-2-yl)-4-hydroxyphenethyl alcohol with mercaptoacetic acid, followed by reaction with m-TMI according to Procedure 10.

Example 40

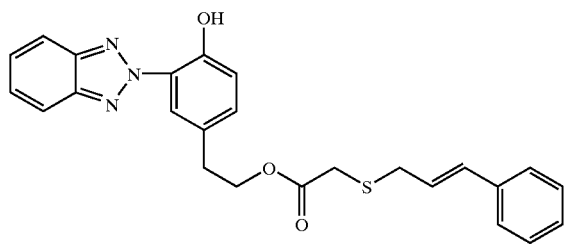

A benzotriazole adduct prepared according to Procedure 8 by the reaction of 3-(2H-benzotriazole-2-yl)-4-hydroxyphenethyl alcohol with mercaptoacetic acid, followed by reaction with cinnamyl chloride according to Procedure 3.

Example 41

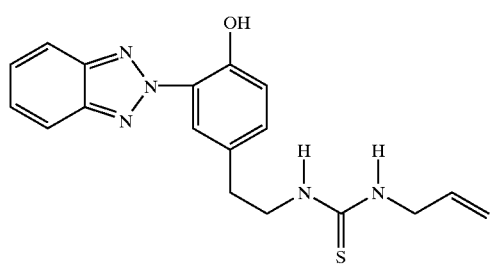

A benzotriazole adduct prepared according to Procedure 5 by the reaction of 3-(2H-benzotriazole-2-yl)-4-hydroxyphenethyl alcohol with methyl sulfonyl chloride and lithium chloride, followed by reaction with ammonia according to Procedure 3. The product, which is a primary amine, is reacted with allylisothiocyanate according to Procedure 11.

Example 42

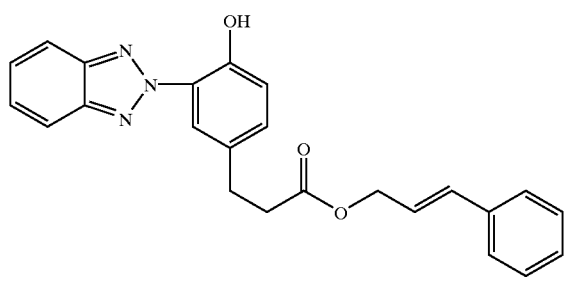

A benzotriazole adduct prepared according to Procedure 8 by the reaction of 2-[2-hydroxy-5-(2-carboxyethyl)phenyl]-2H-benzotriazole (prepared according to L. Stoeber, A. Sustic, W. J. Simonsick, and O. Vogl, *J.M.S.—Pure Appl. Chem.*, A37(9), 943, 2000) with cinnamyl alcohol.

Example 43

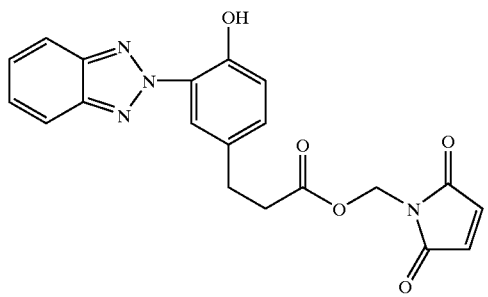

A benzotriazole adduct prepared according to Procedure 8 by the reaction of 2-[2-hydroxy-5-(2-carboxyethyl)phenyl]-2H-benzotriazole (prepared according to L. Stoeber, A. Sustic, W. J. Simonsick, and O. Vogl, *J.M.S.—Pure Appl. Chem.*, A37(9), 943, 2000) with N-methylolmaleimide (prepared according to J. Bartus, W. L. Simonsick, and O. Vogl, *J.M.S.—Pure Appl. Chem.*, A36(3), 355, 1999).

Example 44

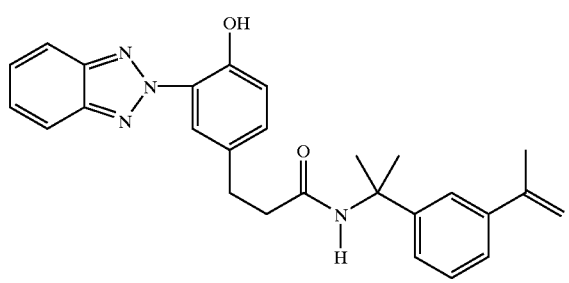

A benzotriazole adduct prepared according to Procedure 13 by the reaction of 2-[2-hydroxy-5-(2-carboxyethyl)phenyl]-2H-benzotriazole (prepared according to L. Stoeber, A. Sustic, W. J. Simonsick, and O. Vogl, *J.M.S.—Pure Appl. Chem.*, A37(9), 943, 2000) with m-TMI.

Example 45

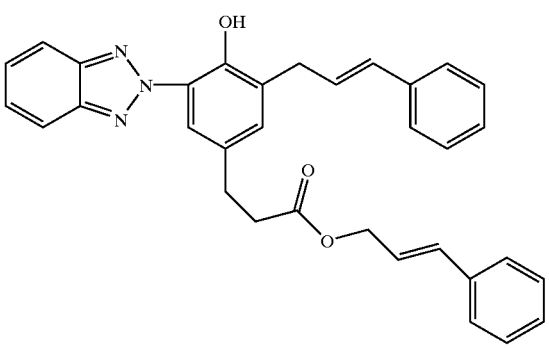

A benzotriazole adduct prepared according to Procedure 20 by the reaction of 2-[2-hydroxy-5-(2-carboxyethyl)phenyl]-2H-benzotriazole (prepared according to L. Stoeber, A. Sustic, W. J. Simonsick, and O. Vogl, *J.M.S.—Pure Appl Chem.*, A37(9), 943, 2000) with cinnamyl alcohol, followed by reaction with another molecule of cinnamyl alcohol according to Procedure 8.

Example 46

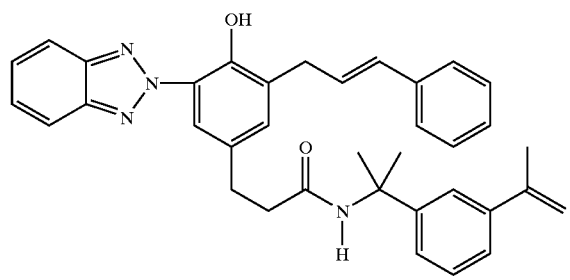

A benzotriazole adduct prepared according to Procedure 20 by the reaction of 2-[2-hydroxy-5-(2-carboxyethyl)phenyl]-2H-benzotriazole (prepared according to L. Stoeber, A. Sustic, W. J. Simonsick, and O. Vogl, *J.M.S.—Pure Appl. Chem.*, A37(9), 943, 2000) with cinnamyl alcohol, followed by reaction with m-TMI according to Procedure 13.

Example 47

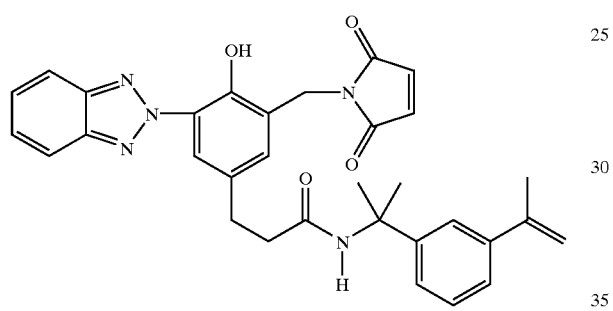

A benzotriazole adduct prepared according to Procedure 20 by the reaction of 2-[2-hydroxy-5-(2-carboxyethyl)phenyl]-2H-benzotriazole (prepared according to L. Stoeber, A. Sustic, W. J. Simonsick, and O. Vogl, *J.M.S.—Pure Appl. Chem.*, A37(9), 943, 2000) with N-methylolmaleimide, followed by reaction with m-TMI according to Procedure 13.

Example 48

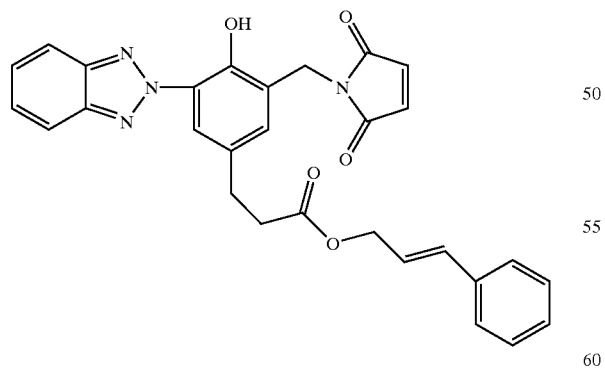

A benzotriazole adduct prepared according to Procedure 20 by the reaction of 2-[2-hydroxy-5-(2-carboxyethyl)phenyl]-2H-benzotriazole (prepared according to L. Stoeber, A. Sustic, W. J. Simonsick, and O. Vogl, *J.M.S.—Pure Appl. Chem.*, A37(9), 943, 2000) with cinnamyl alcohol, followed by reaction with m-TMI according to Procedure 8.

Example 49

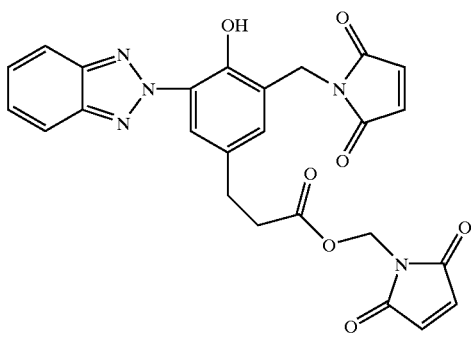

A benzotriazole adduct prepared according to Procedure 20 by the reaction of 2-[2-hydroxy-5-(2-carboxyethyl)phenyl]-2H-benzotriazole (prepared according to L. Stoeber, A. Sustic, W. J. Simonsick, and O. Vogl, *J.M.S.—Pure Appl. Chem.*, A37(9), 943, 2000) with N-methylolmaleimide, followed by reaction with another molecule of N-methylolmaleimide according to Procedure 8.

Example 50

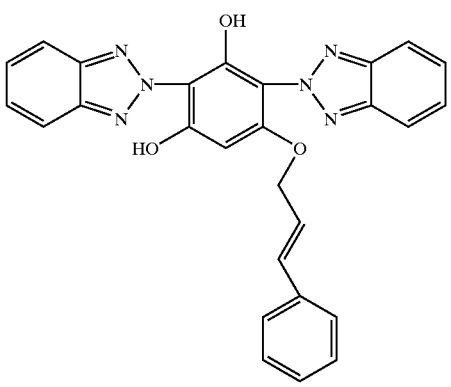

A benzotriazole adduct prepared according to Procedure 16 by the reaction of 2-(2,4,6-trihydroxyphenyl)-1,3-di-(2H-benzotriazole) (prepared according to S. Li and O. Vogl, *Ploymer Bulletin*, 12, 375, 1984) with cinnamyl chloride.

Example 51

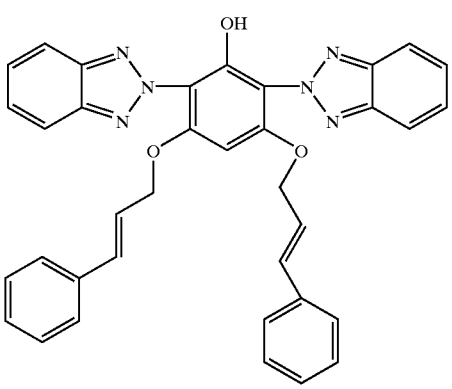

A benzotriazole adduct prepared according to Procedure 16 by the reaction of 2-(2,4,6-trihydroxyphenyl)-1,3-di-(2H-benzotriazole) (prepared according to S. Li and O. Vogl, *Ploymer Bulletin*, 12, 375, 1984) with cinnamyl chloride.

Example 52

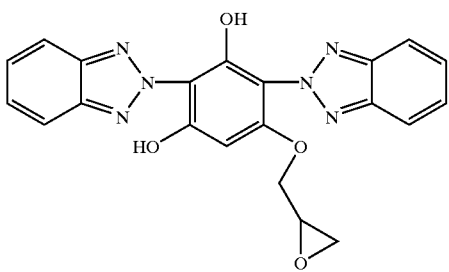

A benzotriazole adduct prepared according to Procedure 16 by the reaction of 2-(2,4,6-trihydroxyphenyl)-1,3-di-(2H-benzotriazole) (prepared according to S. Li and O. Vogl, *Ploymer Bulletin*, 12, 375, 1984) with epichlorohydrin.

Example 53

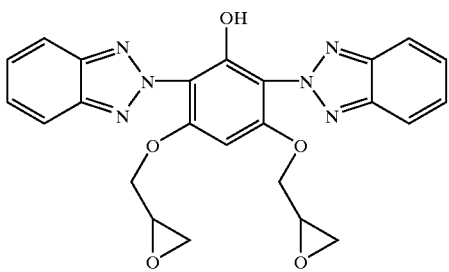

A benzotriazole adduct prepared according to Procedure 16 by the reaction of 2-(2,4,6-trihydroxyphenyl)-1,3-di-(2H-benzotriazole) (prepared according to S. Li and O. Vogl, *Ploymer Bulletin*, 12, 375, 1984) with epichlorohydrin.

Example 54

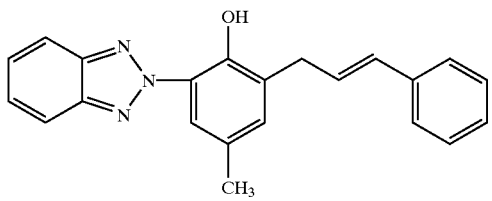

A benzotriazole adduct prepared according to Procedure 20 by the reaction of 2-(2-hydroxy-5-methylphenyl)-2H-benzotriazole with cinnamyl alcohol.

Example 55

Performance of benzotriazole adducts in adhesive compositions. As a control, an adhesive formulation was prepared comprising a bismaleimide, a compound with cinnamyl functionality, an epoxy, curing agents, and 75% by weight silver. Benzotriazole compounds (including a commercially available material as a control, the adducts from Examples 1, 2, and 3, and an adduct containing siloxane as the E group) were added to this composition and the individual compositions tested for adhesive strength as die attach adhesives.

The adhesive was dispensed on a copper coated leadframe with a die pad, 650×650 mil. A silicon die, 500×500 mil, was placed onto the adhesive and the adhesive was cured, either in an oven at 175° C. for 30 minutes, or on a hot plate ("snap cure") at 200° C. for one minute. The cured assemblies were then subjected to 85° C./85% relative humidity for 48 hours, after which the die was sheared from the copper leadframe at 90 degrees with a Dage 2400-PC Die Shear Tester at 260° C.

Ten assemblies for each adhesive composition were tested and the average given in Kilogram force as the result. The results are set out in the following table and show that the addition of a commercially available benzotriazole containing acrylate functionality (Janssen Phamaceutica, NORBLOC) reduces the die shear strength of the base composition containing no antioxidant, but that the addition of the inventive benzotriazole adducts gives a significant improvement.

| Benzotriazole and Amount added to adhesive composition | Die Shear Strength at 260° C. on Cu in Kg After 85° C./85% RH for 48 hours | |
|---|---|---|
| | Oven Cure 30 min 175° C. | Snap Cure 1 min 200° C. |
| None | 11.4 | 8.3 |
| NORBLOC 7966 0.3 wt % | 11.3 | 3.8 |
| Adduct from Ex. 1 0.3 wt % | 32.6 | 15.8 |
| Adduct from Ex. 1 1.0 wt % | 32.6 | 15.2 |
| Adduct with siloxane 0.3 wt % | 45.4 | 28.5 |
| Adduct with siloxane 1.0 wt % | 34.6 | 21.5 |
| Adduct from Ex. 2 0.3 wt % | 48.2 | 19.5 |
| Adduct from Ex. 3 0.3 wt % | 29.1 | 11.7 |
| Adduct from Ex. 3 1.4 wt % | 22.5 | 10.1 |
| Adduct from Ex. 3 2.6 wt % | 17.0 | 6.8 |

Example 56

Performance of benzotriazole adducts as coating on copper surfaces. Copper leadframes were dipped into a solution of a benzotriazole compound, at a concentration of 1%–2% by weight in toluene, were air-dried and then cured for 30 minutes at 120° C. The leadframes (die pad, 650×650 mil) were then used as the substrate for a silicon die, 500×500 mil.

An adhesive formulation (without benzotriazole) was prepared comprising a bismaleimide, a compound with cinnamyl functionality, an epoxy, curing agents, and 75% by weight silver as in the base formulation in Example 55. The adhesive was dispensed on the leadframe, the silicon die placed onto the adhesive, and the adhesive cured, in an oven at 175° C. for 30 minutes. The cured assemblies were then subjected to 85° C./85% relative humidity for 48 hours, after which the die was sheared from the copper leadframe at 90 degrees with a Dage 2400-PC Die Shear Tester at 260° C.

Ten assemblies for each benzotriazole coating composition were tested and the average given in Kilogram force as the result. The results are set out in the following table and show that the use of the commercially available benzotriazole with acrylate functionality (Janssen Phamaceutica, NORBLOC) as a coating composition for copper leadframes reduces the die shear strength of the base composition containing no antioxidant, but that the coating with the inventive benzotriazole adducts gives a significant improvement in three out of the four compositions tested.

| Benzotriazole coating on copper leadframe Wt % in solvent | Die Shear Strength in Kg at 260° C. on Cu |
|---|---|
| None | 25.2 |
| NORBLOC 7966 2 wt % toluene | 19.5 |
| Adduct from Ex. 1 2 wt % toluene | 40.6 |
| Adduct with siloxane 1 wt % toluene | 41.8 |
| Adduct from Ex. 2 2 wt % toluene | 14.4 |
| Adduct from Ex. 4 1 wt % methanol | 35.2 |

What is claimed:

1. A benzotriazole adduct having the structure:

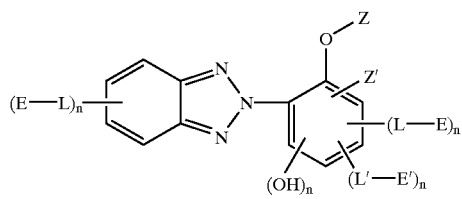

in which n is 0, 1, 2, or 3;

E and E' independently are an organic moiety containing vinyl, ether, vinyl silane, carbon to carbon double bond attached to an aromatic ring and conjugated with the unsaturation in the aromatic ring, epoxy, acetyl acetonate, fumarate, maleate, or maleimide functionality;

Z is hydrogen, hydrocarbyl, or an organic moiety containing electron donor, epoxy, acetyl acetonate, or electron acceptor excluding acrylate, functionality;

Z' is hydrogen, hydrocarbyl, an electron donating group, or an electron withdrawing group, L and L' independently are a hydrocarbyl group, or a functionality selected from the group consisting of:

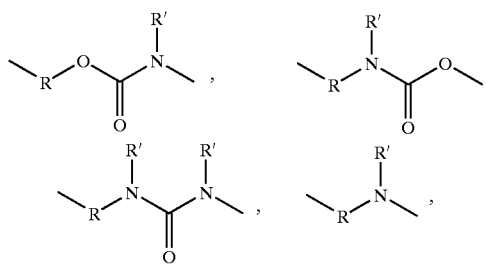

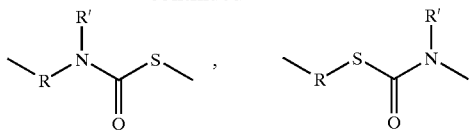

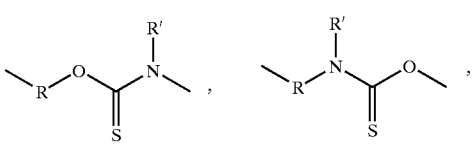

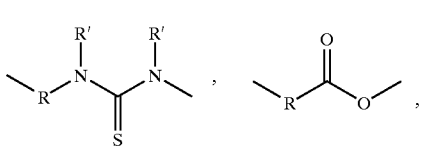

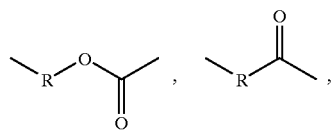

in which R is a hydrocarbyl group attached to the benzotriazole segment; and R' is hydrogen, an aromatic, or an alkyl group of 1 to 6 carbon atoms, and provided that if n is 0 for each of (E-L), (L-E), or (L'-E'), then Z is not hydrogen or alkyl; and provided that if L or L' is alkyl and E is a maleimide or a styrene group, then for (L-E) or (L'-E'), n must be more than 1, or for (E-L), n must be at least one.

2. The benzotriazole adduct according to claim 1 in which n is 0 for (E-L), (L'-E') and for (OH), Z is hydrogen, Z' is hydrogen; n is 1for (L-E), and L is not alkyl.

3. The benzotriazole adduct according to claim 1 in which n is 0 for (E-L), (L'-E'), and for (OH), n is 1 for (L-E), L is not alkyl, Z is an organic moiety containing electron donor, epoxy, vinyl, acetyl acetonate, or electron acceptor excluding acrylate, functionality; and Z' is hydrogen.

4. The benzotriazole adduct according to claim 1 in which n is 0 for (E-L) and (L'-E'), n is 2 for (L-E), Z is hydrogen ; and Z' is hydrogen.

5. The benzotriazole adduct according to claim 1 having the structure:

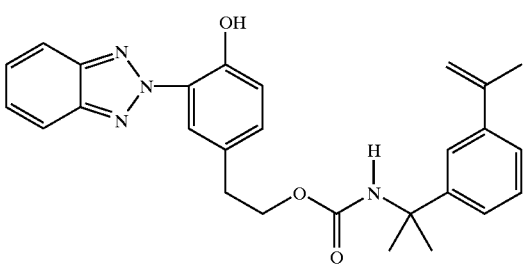

6. The benzotriazole adduct according to claim 1 having the structure:

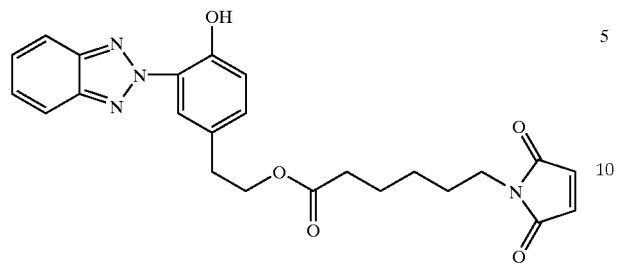

7. A benzotriazole adduct having the structure:

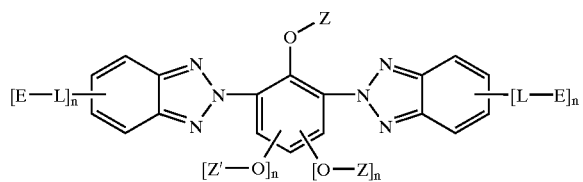

in which n is 0, 1, 2, or 3;

E and E' independently are an organic moiety containing vinyl, ether, vinyl silane, carbon to carbon double bond attached to an aromatic ring and conjugated with the unsaturation in the aromatic ring, epoxy, acetyl acetonate, fumarate, maleate, or maleimide functionality;

Z is hydrogen, hydrocarbyl, or an organic moiety containing electron donor, epoxy, acetyl acetonate, or electron acceptor excluding acrylate, functionality;

Z' is hydrogen, hydrocarbyl, an electron donating group, or an electron withdrawing group, at least one of Z and Z' cannot be hydrogen or alkyl;

L and L' independently are a hydrocarbyl group, or a functionality selected from the group consisting of:

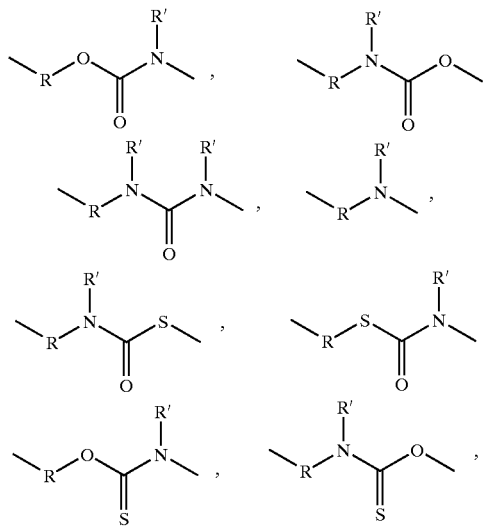

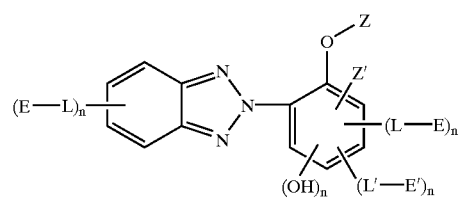

in which in which R is a hydrocarbyl group attached to the benzotriazole segment; and R' is hydrogen, an aromatic, or an alkyl group of 1 to 6 carbon atoms.

8. A curable composition comprising a benzotriazole adduct, optionally a curing agent, and optionally a filler, the benzotriazole adduct having the structure

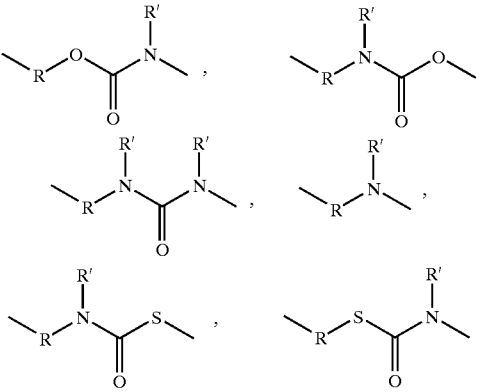

in which n is 0, 1, 2, or 3;

E and E' independently are an organic moiety containing vinyl ether, vinyl silane, carbon to carbon double bond attached to an aromatic ring and conjugated with the unsaturation in the aromatic ring, fumarate, maleate, maleimide, epoxy, vinyl, acetyl acetonate, (meth)acrylate, (meth)acryl amino, glycidyl, or siloxane functionality;

Z is hydrogen, hydrocarbyl, or an organic moiety containing electron donor, epoxy, vinyl, acetyl acetonate, (meth)acrylate, (meth)acryl amino, glycidyl, or siloxane functionality;

Z' is hydrogen, hydrocarbyl, an electron donating group, or an electron withdrawing group, L and L' independently are a hydrocarbyl group, or a functionality selected from the group consisting of:

-continued

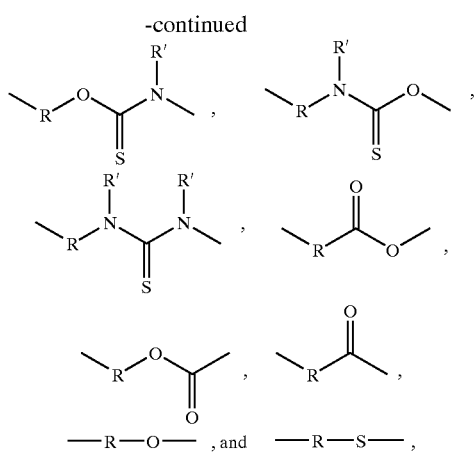

in which R is a hydrocarbyl group attached to the benzotriazole segment; and R' is hydrogen, an aromatic, or an alkyl group of 1 to 6 carbon atoms.

9. A curable composition comprising a benzotriazole adduct, optionally a curing agent, and optionally a filler, the benzotriazole adduct having the structure

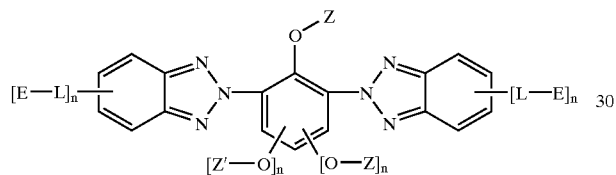

in which

E and E' independently are an organic moiety containing vinyl ether, vinyl silane, carbon to carbon double bond attached to an aromatic ring and conjugated with the unsaturation in the aromatic ring, fumarate, maleate, maleimide, epoxy, vinyl, acetyl acetonate, (meth) acrylate, (meth)acryl amino, glycidyl, or siloxane functionality;

Z is hydrogen, hydrocarbyl, or an organic moiety containing electron donor, electron acceptor, epoxy, vinyl, acetyl acetonate, (meth)acrylate, (meth)acryl amino, glycidyl, or siloxane functionality;

Z' is hydrogen, hydrocarbyl, an electron donating group, or an electron withdrawing group, L and L' independently are a hydrocarbyl group, or a functionality selected from the group consisting of:

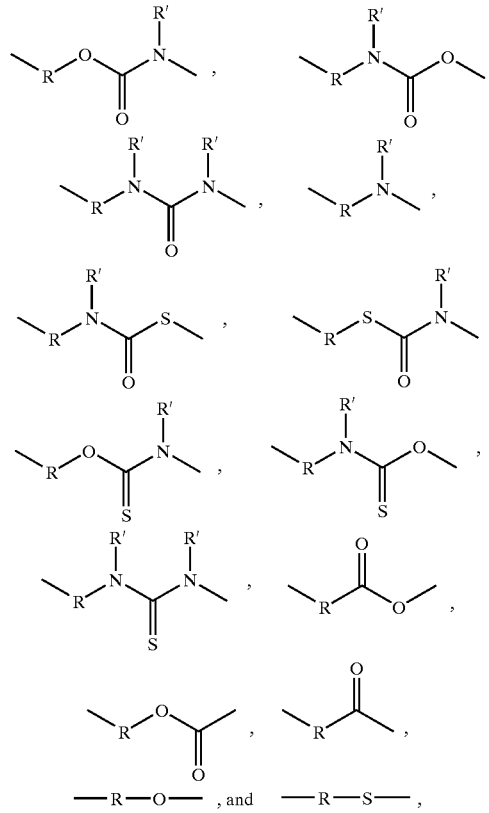

in which R is a hydrocarbyl group attached to the benzotriazole segment; and R' is hydrogen, an aromatic, or an alkyl group of 1 to 6 carbon atoms.

* * * * *